(12) United States Patent
DeLuca et al.

(10) Patent No.: US 6,440,067 B1
(45) Date of Patent: Aug. 27, 2002

(54) SYSTEM AND METHOD FOR REMOTELY MONITORING FUNCTIONAL ACTIVITIES

(75) Inventors: Carlo J. DeLuca, Wellesley; Serge H. Roy, Duxbury, both of MA (US)

(73) Assignee: Altec, Inc., Boston, MA (US)

( * ) Notice: Subject to any disclaimer, the term of this patent is extended or adjusted under 35 U.S.C. 154(b) by 0 days.

(21) Appl. No.: 09/513,942

(22) Filed: Feb. 28, 2000

(51) Int. Cl.$^7$ ................................................ A61B 5/00
(52) U.S. Cl. ........................ 600/300; 600/546; 128/920; 128/925
(58) Field of Search .................. 706/924; 600/300–301, 600/500–508, 529–538, 544–545, 554–556, 585–595; 128/900, 903–904, 920–925; 434/265

(56) References Cited

U.S. PATENT DOCUMENTS 5,442,729 A * 8/1995 Kramer ....................... 128/925
6,244,873 B1 * 6/2001 Hill et al. .................... 600/595

* cited by examiner

*Primary Examiner*—Kevin Shaver
*Assistant Examiner*—Michael C. Astorino
(74) *Attorney, Agent, or Firm*—John E. Toupal; Harold G. Jarcho (57) ABSTRACT

A method for remotely monitoring and identifying Functional Activities performed by a test subject, the method including the steps of (a) extracting a given type of signals from each of a predetermined set of muscles of a control subject during the performance thereby of a given Functional Activity; (b) processing the signals to provide therefor given parameters affected by the given Functional Activity; (c) storing the data obtained in step (b); and (d) repeating steps (a)–(c) for a plurality of other control subjects. The stored data then is utilized to establish a normative data base indicative of the given Functional Activity and further steps include (f) extracting the given type of signals from each of at least some of the predetermined set of muscles of a test subject during a given monitoring period; and (g) comparing the data base to the signals of step (f) to identify during the monitoring period portions thereof during which the test subject was performing the given Functional Activity.

44 Claims, 7 Drawing Sheets

DEVELOPMENT PHASE

MONITORING PHASE

SYSTEM AND METHOD FOR REMOTELY MONITORING FUNCTIONAL ACTIVITIES

BACKGROUND OF THE INVENTION

The present invention relates to a computer-based method and system for remotely monitoring physical activity in a continuous and unobtrusive fashion while an individual performs normal and usual activities of daily living.

With continuing emphasis placed on the financial management of health care, it is inevitable that a growing number of patients in need of physical rehabilitation will be channeled to receive a significant part of their rehabilitation in the home. This trend is both financially as well as practically driven to ensure that the limited available resources are used effectively. It also focuses care towards independent functioning at home or under assisted-living conditions rather than extended institutional care or overuse of clinical services.

Health providers need condensed and specific information to describe the physical and functional performance of their patients in the home or other remote location, without relying on self-reports or having the patient leave the home. For example, objective parametric measures are needed to describe how physically active the patient has been, and the type and degree of activities of daily living (such as walking, stairclimbing, feeding, grooming, dressing, exercise, etc.) he/she has performed during a specified period of time. Having this information readily available to the health provider can augment clinical service by making the home a more effective place for rehabilitation, especially for the elderly patient, or person with neurological disorders.

At last two groups of patients can benefit from home-based monitoring of Functional Activities. The first consists of those patients who are discharged to the home setting after inpatient rehabilitation. The current model of care relies on regular updates of a patient's functional status. These updates are currently provided on a relatively infrequent basis and are often based on self-reports or limited observation of the patient's activity. Self-reports can be vague or inaccurate due to poor memory or misconceptions, or biased by the variable amount of assistance provided. Observer rated surveys are often time consuming and do not reflect changes in performance that may occur during the patient's day. A second group of patients that can benefit from home-based monitoring of Functional Activities are those "at risk" of significant functional decline. These patients are typically followed as outpatients in hospital based clinics, or are followed through home care services. Both approaches to care have significant drawbacks. The hospital based approach typically consists of relatively infrequent visits that are often inconvenient for the patient and are expensive for the health care system. This approach also has the disadvantage of taking the patient out of their usual environment so that information about functional abilities is based on self-report or on a limited functional examination in the hospital setting, which typically does not adequately approximate the patient's own home environment. The home-based approach is also expensive and typically involves limited observation of the patient's functional performance for a period of several hours per day, often limited to less than 5 days per week. Decisions about increasing or decreasing the amount of services are thus based on a limited data set that may not reflect the patient's true abilities and needs.

By monitoring a patient in "real time", adjustments to the patient's support services can be made quickly. This approach has the obvious advantage of providing the appropriate amount of assistance required. It also has the potential to significantly reduce costs of care, by providing assistance as soon as it is required, rather than waiting for the deleterious effects of a person's inability to care for themselves to manifest as poor nutrition or hygiene. When these conditions occur, the patient often re-enters the inpatient health care system. When the ultimate outcome is institutionalization, the quality of life decreases and the cost of care goes up substantially. Measuring a patient's true performance of functional motor tasks automatically in the home would provide a means for assessing the extent to which a patient is able to provide their own self-care. For example, a patient who is physically able to perform their activities of daily living with supervision or cueing might not actually perform them if left on their own. In the current system of care, such a patient would likely receive fewer services than would actually be required. Only when the results of a lack of appropriate self-care become apparent would the amount of services be re-evaluated.

The object of the present invention, therefore, is to provide a system for monitoring remotely the amount and kinds of physical activity that a patient or other user conducts throughout a given time period.

SUMMARY OF THE INVENTION

The invention is a method for remotely monitoring and identifying Functional Activities performed by a test subject, the method includes the steps of (a) extracting a given type of signals from each of a predetermined set of muscles of a control subject during the performance thereby of a given Functional Activity; (b) processing the signals to provide therefor given parameters affected by the given Functional Activity; (c) storing the data obtained in step (b); and (d) repeating steps (a)–(c) for a plurality of other control subjects. The stored data then is utilized to establish a normative data base indicative of the given Functional Activity and further steps include: (f) extracting the given type of signals from each of at least some of the predetermined set of muscles of a test subject during a given monitoring period; and (g) comparing the data base to the signals of step (f) to identify during the monitoring period portions thereof during which the test subject was performing the given Functional Activity. The method can be used unobtrusively in a home environment to monitor the degree and type of motor activity of various test subjects.

According to one feature of the invention, step (e) includes passing the data through a classification algorithm to identify specific signal patterns which correspond to the given Functional Activity. Identification of useful signal patterns is facilitated with the use of algorithms.

According to another feature, the muscle includes a predetermined number of muscles, step (e) includes identifying for the data base those signals extracted from a portion of the muscles having patterns most dependent on the given Functional Activity, and step (f) comprises extracting the signals only from that portion of the muscles. This feature improves response time of the method.

According to other features of the invention, the signals are biosignals, preferably Electromyographic (EMG) signals and the given parameters include at least some taken from a group including root-mean square value, envelope, mean rectified value and frequency characteristics. These features provide data highly effective in Functional Activity identification.

According to still other features of the invention, step (a) includes attaching a sensor over each of the muscles which include either the Deltoid and the Erector Spinae, the Erector Spinae and a muscle in the front portion of the subject's thigh, or the Deltoid, Erector Spinae and Vastus Lateralis. A large number of Functional Activities can be monitored using these featured muscles.

According to a further feature, the method includes the step of transmitting data representing the Functional Activities of the test subject between a location occupied thereby and a remote location for evaluation by testing personnel. This feature facilitates monitoring of a test subject by remotely located testing personnel.

According to an additional feature of the invention, the algorithm includes a Neural Network or Fuzzy Logic technique both of which are particularly effective in establishing useful data bases.

According to an important feature of the invention, step (a) above includes extracting the signals from a plurality of different sets of muscles of control subjects during the performance of a variety of Functional Activities; step (b) includes determining for the signals distinct given parameters which identify each of the Functional Activities; step (e) includes establishing a plurality of normative data bases each indicative of a different one of the Functional Activities; and step (f) includes extracting the signals from each of at least some of the muscles of each set. Subsequently, step (g) can include comparing the data bases to the signals of step (f) to identify during the monitoring period portions thereof during which said test subject was performing each of the Functional Activities.

Also encompassed by the invention is a method for remotely monitoring and identifying Functional Activities performed by a test subject including the steps of (a) extracting a given type of signals from each of a predetermined set of muscles of the test subject during the performance thereby of a given Functional Activity; (b) processing the signals to provide for the signals given parameters affected by the given Functional Activity; (c) storing data obtained in step (b); (d) utilizing the data stored in step (c) to establish a normative data base indicative of the given Functional Activity; (e) extracting the given type of signals from at least some of the predetermined set of muscles of the test subject during a given monitoring period; and (f) comparing the data base to the signals of step (e) to identify during the monitoring period portions thereof during which the test subject was performing the given Functional Activity. This method facilitates activity monitoring of test subjects having abnormalities of motor function.

Additionally encompassed by the invention is a system for remotely monitoring and identifying Functional Activities performed by a test subject and including a plurality of sensors for providing signals in response to muscle activity, the sensors adapted for placement to extract the signals from predetermined muscles of the test subject; a processor for determining certain parameters of the signals; a computer programmed with a data base cataloging different patterns of the parameters each produced by a different Functional Activity of the test subject, the computer being adapted to compute during a given monitoring period those portions thereof during which the test subject was performing each of the different Functional Activities; and a transmission system for transmitting data representing the Functional Activities performed by the test subject between a location occupied by the test subject and a remote location for evaluation by testing personnel. The system permits unobtrusive, remote monitoring of physical activities of a test subject.

According to certain features of the system, the sensors are adapted for attachment to the test subjects skin portions overlying the muscles, a processor is carried by each sensor, the computer is in the location occupied by the test subject, and the system includes a repeater carried by the test subject and functional to transmit signals between the sensors and the computer. These features allow free movement of the test subject during a monitoring period.

According to another feature of the system, the transmission system is a telephone and/or Internet link between the computer means and the remote location. The telephone and/or Internet link efficiently establishes communication between the subject and the remote location.

DESCRIPTION OF THE DRAWINGS

These and other objects and features of the invention will become more apparent upon a perusal of the following description taken in conjunction with the accompanying drawings wherein.

DESCRIPTION OF THE PREFERRED EMBODIMENTS

Figure 1:
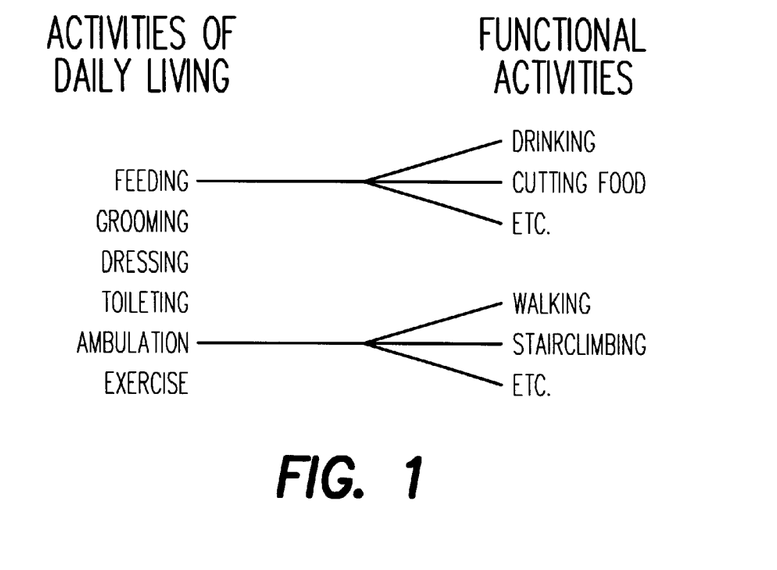
FIG. 1 is a diagram representing different activities of daily living and how each of these activities are comprised of different Functional Activities.
Figure 2A:
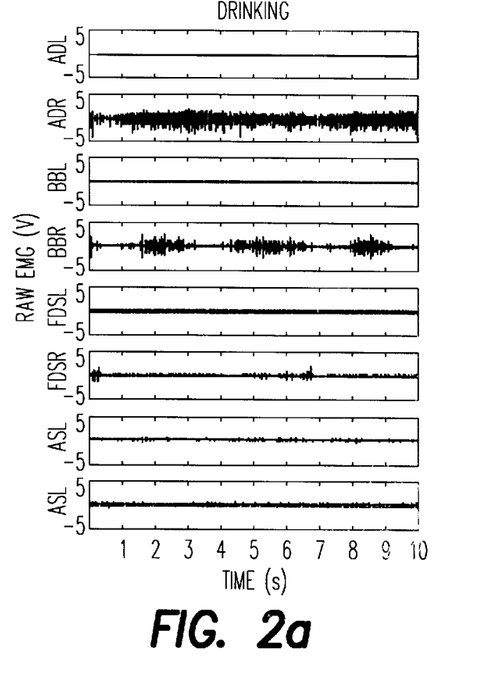
FIGS. 2a–2d are plots of raw EMG signals taken from a subject performing various Functional Activities.
Figure 2B:
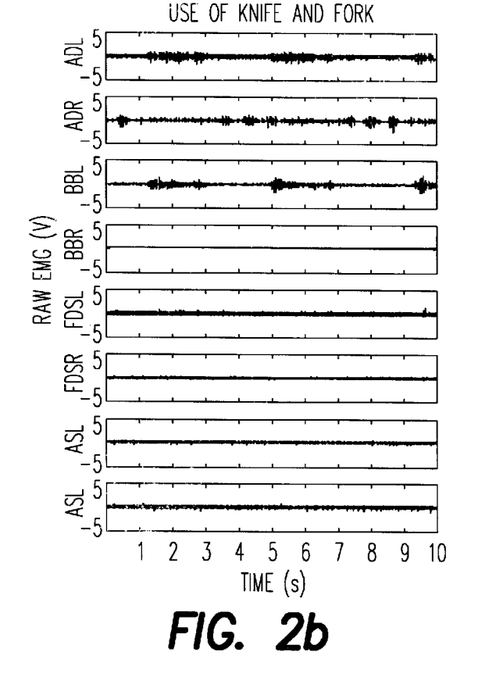
Figure 2C:
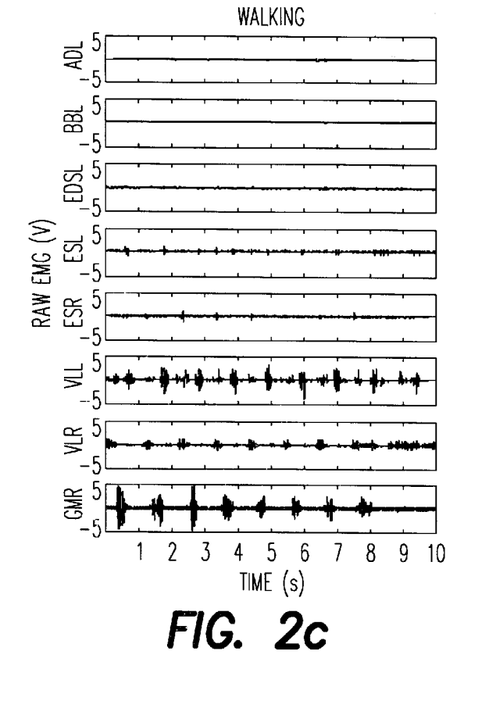
Figure 2D:
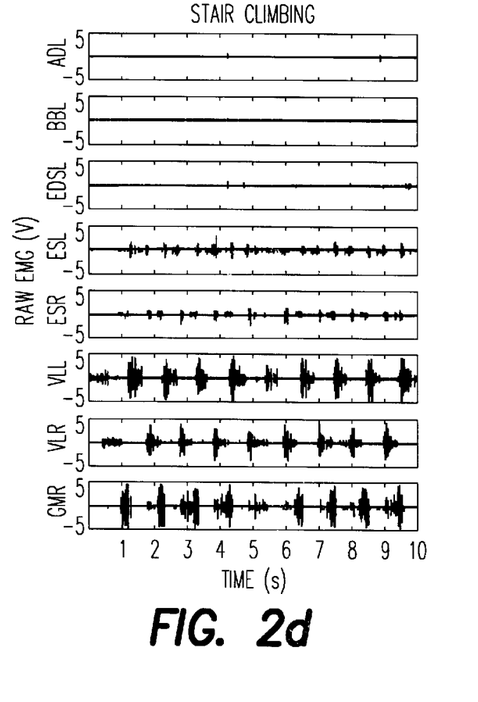

For purposes of the invention, Functional Activities are defined as purposeful activities which an individual typically performs during normal daily living. They include, for example, such general activities as feeding, dressing, grooming, toileting, ambulating, exercising, and the like. As depicted in FIG. 1, each of the activities of daily living can be further categorized into specific Functional Activities. Examples of Functional Activities needed for feeding are drinking from a cup, or cutting food with a fork and knife; examples of Functional Activities during ambulating are walking on level ground and climbing stairs. Motor tasks, or ordered sequences of joint movements and corresponding muscle activities needed to perform a specific Functional Activity, are different for each Functional Activity. Different motor tasks produce different sequences and magnitudes of muscle activity, which can be recorded by acquiring signals from the muscles of the body during the performance of the Functional Activity.

For example, the surface electromyographic (EMG) signal is the electrical activity detected at the surface of the skin that arises from the complex set of events involved in muscle contraction. There is a direct relationship between the forces produced by a muscle and the amplitude of the EMG signal. The basis for this relationship is that the strategies used by the nervous system to increase the amount of force produced by a muscle, i.e. a recruitment of more muscle fibers and an increase in their rate of activation, also result in an increase in the amount of electrical activity produced by the muscle when it contracts. A more detailed description of the relationship between muscle force production and characteristics of the EMG signal are described in the test, "Muscles Alive" by Basmajian and DeLuca, 1985.

The resultant recording of superimposed "raw" EMG signals from different muscles during the performance of a Functional Activity describes a pattern that is characteristic for that particular activity. Examples of such patterns are depicted in FIGS. 2a–2d where raw EMG signal data from eleven muscles of the body are shown while the same subject was feeding himself (drinking from a cup (FIG. 2a); cutting food (FIG. 2b)) and ambulating (walking on level ground (FIG. 2c); stairclimbing (FIG. 2d)). Muscles used were the Left Anterior Deltoid (ADL), Right Anterior Deltoid (ADR), Left Biceps Brachii (BBL), Right Biceps Brachii (BBR), Left Flexor Digitorium Superficialis (FDSL), Right Flexor Digitorium Superficialis (FDSR), Left Erector Spinae (ESL), Right Erector Spinae (ESR), Left Vastus Lateralis (VLL), Right Vastus Lateralis (VLR), Right Medial Gastrocnemius (GMR). The Functional Activities can be distinguished in the examples by visual inspection of the characteristically different EMG signal patterns. A more precise and objective way of identifying the pattern of EMG activity corresponding to a specific Functional Activity is by extracting feature-parameters of the signals from each of the muscles, such as the differences in timing, the amplitude and frequency characteristics of the signals, and processing this information by mathematical methods of pattern recognition.

Figure 3:
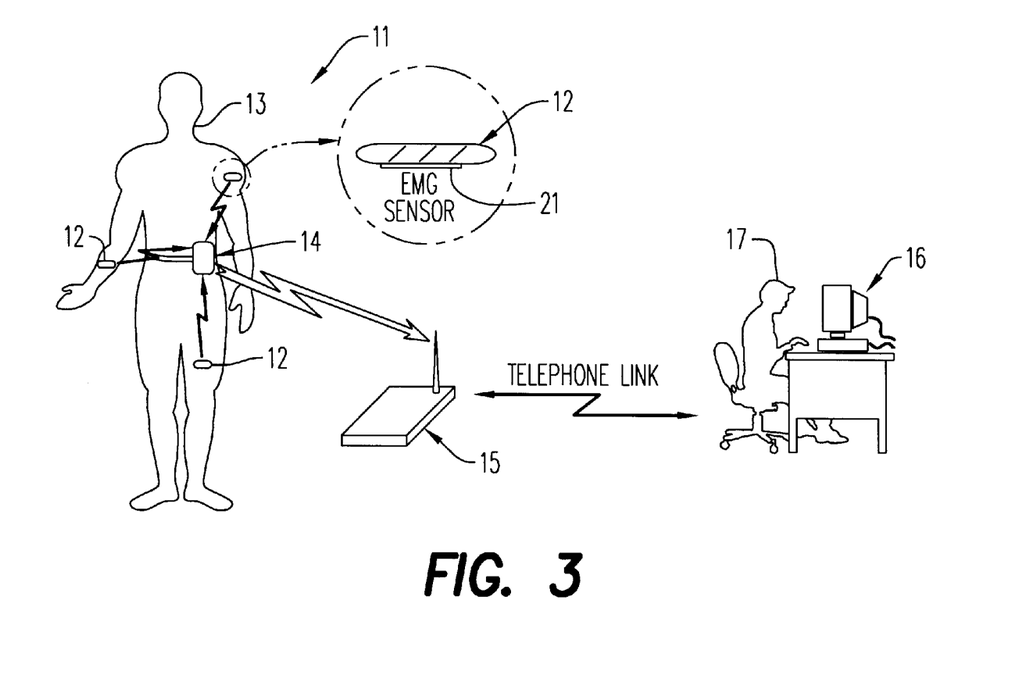
FIG. 3 is a schematic representation of a tele-monitoring system of the invention.

A preferred embodiment of the invention encompasses a computer based system 11 illustrated in FIG. 3 and including hardware and software elements for acquiring and processing surface EMG signals for the purpose of Functional Activity identification. Wireless sensors 12 are attached to the skin of a subject 13 above muscles of interest to extract and condition the EMG signals, and transmit them to a body-worn transceiver 14 (Repeater) which further conditions and relays the signal to a base station 15 at the location occupied by the subject 13. The base station processes the signals for classification of Functional Activities using an algorithm function trained to recognize patterns of EMG activity that correspond to specific Functional Activities representative of standardized activities of daily living. Specific and general data representing the amount and kinds of Functional Activities is transmitted by the base station 15 to a remote location having a computer 16. Transmission can be via telephone lines or the Internet. At the remote location, the data can be retained in patient records by a physician, health care provider, or other testing personnel 17.

Figure 4:
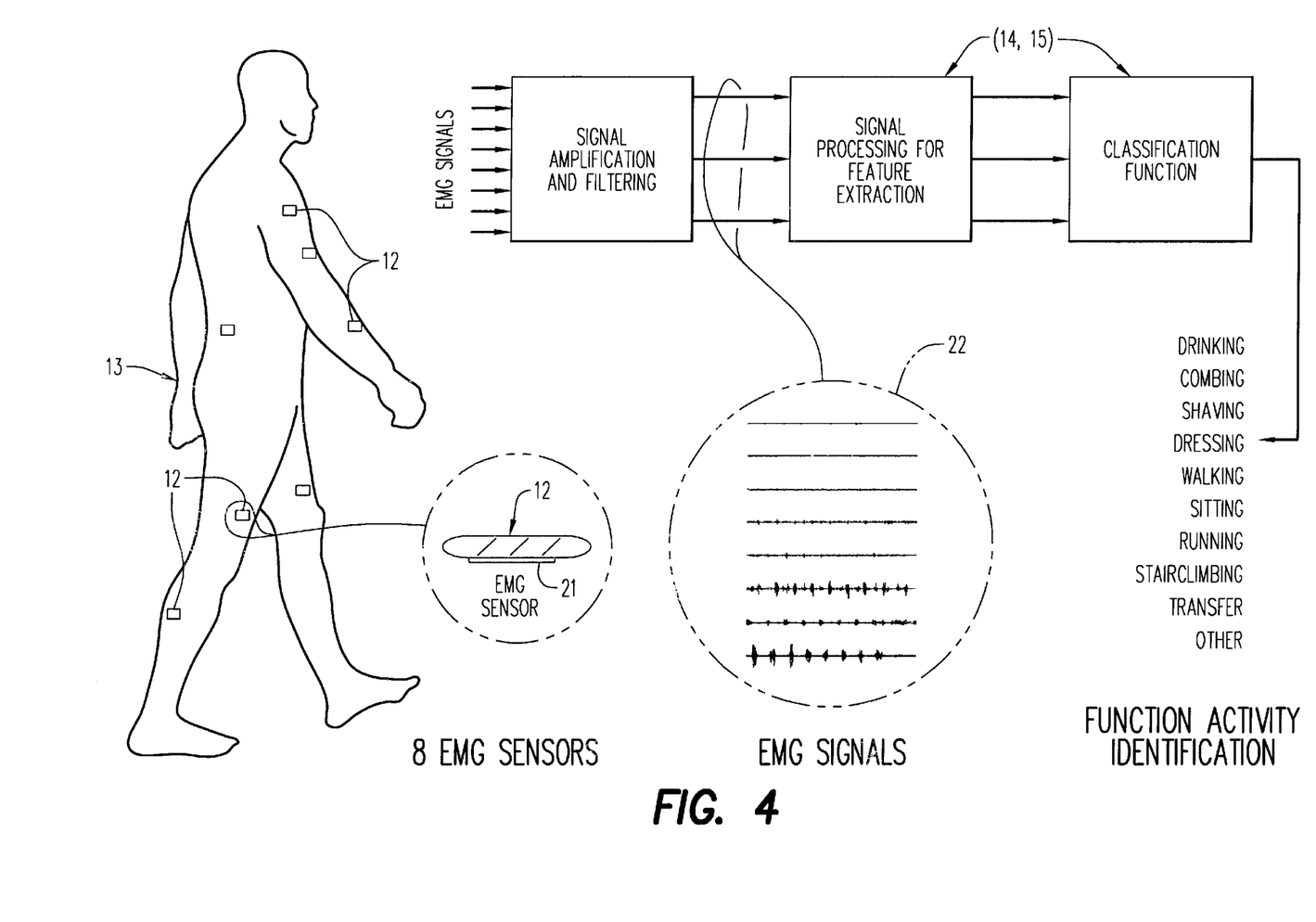
FIG. 4 is a schematic representation depicting the use of the system of FIG. 3 to monitor one of the many Functional Activities (walking) performed during activities of daily living.

Referring now to FIG. 4, the organization and processing of EMG signals for the preferred embodiment are shown illustrated under normal use. The subject 13 generates physiologic signals from the muscles during walking, a Functional Activity that is representative of the many activities of daily living that can be monitored by the device. The physiological signals are detected by the surface EMG sensors 12, and produce electrical signals which are indicative of the underlying physiological process. After detection, the signals are amplified and filtered by circuits 21 within the sensors 12 which are conventional and of the type, for example, disclosed in U.S. patent application Ser. No. 09/356,856. The extracted time series of the EMG signals from each sensor are referred to as "raw" EMG signals 22 which in FIG. 4 are derived from sensors 12 located over predetermined muscles of a real subject performing a Functional Activity such as walking on a level surface. Amplification of the signals detected at the skin surface is used to increase the magnitude of the signal from a micro-volt (uV) range to a voltage (V) range, and eliminate unwanted common mode signals through a process of differentiation. A high-pass filter, with a corner frequency ranging from 0 to 30 Hz is used to remove motion artifacts and a low-pass filter with a corner frequency ranging from 50 to 1000 Hz is used to remove high-frequency noise contaminating the signal. This filtering operation results in a signal containing information which is representative of muscle activation. The EMG signals then are converted from a continuous or analog form into a digital form so that they can be processed by the base station 15 (FIG. 3) and compared to a data base to perform the pattern recognition and Functional Activity identification. In the preferred embodiment of the device, signal differentiation, filtering, gain, and digitization take place within the sensor 12. The signals are transmitted from the sensor 12, using a low-power radio frequency (RF) transceiver chip to establish a communications link with the body worn repeater 14.

The repeater 14 hardware can include, for example, a transceiver for establishing an RF link with each of the sensors 12, an embedded microcontroller to control low level tasks associated with sensor management, an embedded micro-computer for signal processing and LAN interface, and a wireless LAN transceiver for communication with the home base station 15. Management of the following functions is performed by the microcomputer via a bi-directional RF communications link between each of the sensors in the network: i) identify the sensors in the network and set up network addresses, ii) configure the sensors based on instructions from the microcomputer, and iii) poll the sensors for data. The received data is buffered and transferred to the embedded microcomputer, which will process the data, to extract the desired activity information (i.e. feature extraction) based on the EMG muscle activation patterns. Feature extraction converts the raw EMG data from the sensors to a simplified form where only minimally needed components of the signal are extracted for later input to the classification function. The process of feature extraction in the preferred embodiment of the device will take place through a process of calculating the envelope of the signal, segmenting the envelope into epochs of time, and discretizing the amplitude of the EMG envelope for each epoch. Computer based data acquisition procedures, including methods of feature extraction, are discussed hereinafter.

Alternatively, some functions of the EMG feature extraction can be shared by the hardware configurations provided in the sensor 12, the repeater 13, and the home base station 15. The microcomputer in the body mounted repeater 15 will format the feature extracted information into a standard communication protocol such as IEEE802.11, and control the wireless LAN hardware section for transmission to the base station 15. Overall system design is such that several synchronized sensors can co-exist in a network, sharing the bandwidth of the individual sensors such as amplifier gain, the band pass filter characteristics, the sampling frequency, and signal processing algorithms. The repeater 15 is battery powered and carried on the belt or placed within close proximity (two meters) to the subject 13.

The feature extracted signals from each EMG channel serve as the inputs to the classification functions which are programmed in the microcomputer of the home base station 15 (FIG. 3) and output from the classification function is Functional Activity identification. The home base station 15 would typically be placed in the home environment of the patient or user of the system and connected via phone line to the computer monitoring system 16 remotely located at a health care provider or other intended operator of the system. Essentially, the home base station 15 is in the form of a hand-held style computer. However, to facilitate use by the elderly or infirm, it can be configured with a touch screen display rather than a keyboard, and can be outfitted to provide simple audible instructions to the subject patient. These instructions would include how to attach the sensors 12 to the selected muscle site, and when to remove the sensors to recharge them. Alternatively, instructions could also be provided to assist the patient with specific uses of the system, such as for documenting compliance with a home exercise program which the system could be trained to recognize through the EMG signal patterns detected during the performance of the specific exercises. A separate docking station linked to the base station will serve to recharge the sensors. During recharging, the sensors will be inserted into slots of the docking station where they are recharged using the detection contacts. Such a docking system is disclosed in above noted U.S. patent application Ser. No. 09/356,856.

The following components of the base station 15 will have specific functions: A wireless LAN card is used to communicate data and instructions with the body mounted repeater 14. Low level software controls the wireless LAN card, the touch screen and audio sections, and modem section of the microcomputer. The modem establishes a telecommunications link with the remote computer monitoring station 16 and home base station 15 contains an application program designed for configuring the system for a specific patient monitoring protocol. For instance, if the system is being used to monitor physical activity in subject patients without severe impairments, a generic classification function derived from a normative EMG data base would be programmed for use. Alternatively, if a subject patient has severe neuromuscular impairments that cause him to move in a very atypical manner, then the home base station could be configured through the interactive display to first operate in a training mode, to develop a Functional Activity classification algorithm for that specific patient, prior to the use of the device as a monitoring system. Therefore, the application program on board the home base station 15 coordinates all aspects of the protocol, presents the subject with a graphical interface, processes the received data from the repeater 14 and transfers appropriate information regarding the frequency occurrence and type of performed Functional Activities in a timely manner to the remote computer monitoring station 16.

Alternatively, other embodiments of the device may utilize pre-amplification stages and acquisition circuits for digitizing the data that are separate from the sensor, and the sensors may be tethered electrodes which transfer the data directly via cables, or by the use of transportable memory storage devices, to a personal computer where the processing and presentation of the functional task identification can take place. This information can either be printed online, faxed, or transferred by modem or via the Internet to a remote location.

Figure 7:
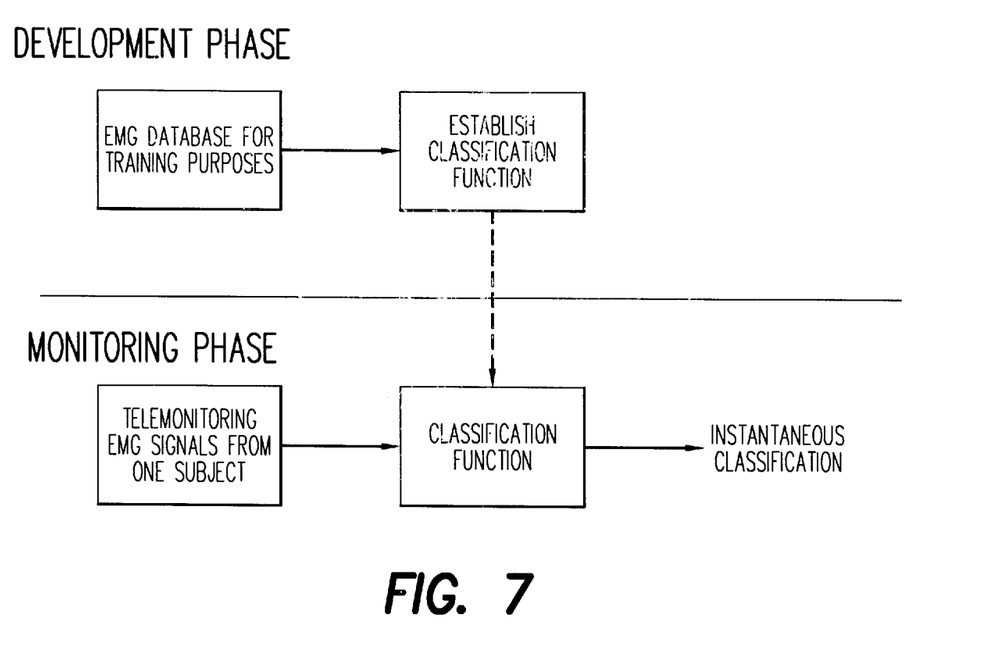
FIG. 7 is a block diagram depicting a training process whereby processing of an EMG database sets a classification function.

The block diagram depicted in FIG. 7 illustrates that the device functions in a monitoring or "real-time" mode, when a classification function is developed and loaded into the system. Classification functions for Functional Activity identification are derived in the preferred embodiment of the device through training of the selected algorithm by an EMG database (FIG. 7). Two general applications of the innovation are described that require different EMG data base structures needed to derive the classification function through training.

As noted above, one application of the system 11 is for monitoring Functional Activities in people with relatively normal motor function; i.e. people without neuromuscular impairments that cause peculiar or highly atypical movements of the body and limbs, such as for example, muscle spasticity and dystonias. When monitoring physical activity in people with relatively normal motor function, the classification function utilized by the system is a function previously developed through the processing of a normative data base of EMG signals indicative of various Functional Activities. The normative data base is developed by acquiring and storing EMG data from among a representative cross-section of control subjects (i.e. young and old; male and female) without neuromuscular impairments or identifiable physical disabilities (referred to as "Normals") during the performance of a variety of Functional Activities. Each of the Functional Activities which the system is trained to identify are performed over a series of repetitions (approximately 100 repetitions ) in order to provide an adequate size data base to train the artificial Neural Network. In an intended embodiment of the system 15 the EMG data base will be comprised of eight channels of EMG signals corresponding to selected sets of muscle recording sites such as those used in FIGS. 2a–2d. One of the functions of the training process is to train a suitable algorithm to perform the Functional Activity identification using four or less of the eight EMG channels from the data base. Upgrades to the classification function can be obtained by testing a larger sampling of normal control subjects and by adding more functional motor tasks to the data base.

A second general application of the system 11 is to monitor Functional Activity in patients with abnormalities of motor function, as for example patients with neuromuscular diseases or disorders. For this application, the classification function derived from the normative data base is not applicable and a patient specific data base is required. Unlike the normative data base, the patient data base is acquired individually and separately for each subject patient prior to its use as a monitoring system. In all other regards, however, the subject patient data base is acquired and processed and stored in the same way as for the normative data base used for normal subjects.

Figure 5:
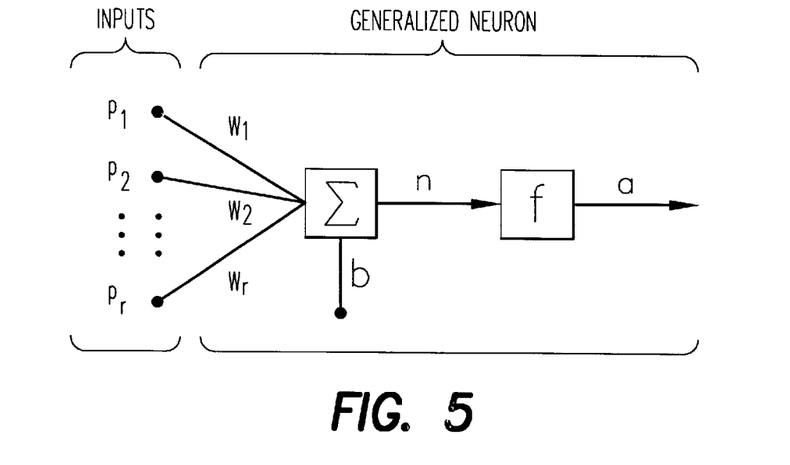
FIG. 5 is a schematic of a single node or neuron of a Neural Network algorithm where:
  p=input to the neuron
  r=total number of inputs
  w=weight (gain) for each input
  b=bias of the neuron
  n=output of the summing junction
  f=transfer function of the neuron
  a=output of the neuron.

A preferred method of pattern recognition incorporated in the present invention as a computer program is the artificial Neural Network. (The theory of Neural Nets is discussed fully in "Understanding Neural Networks and Fuzzy Logic" by S. V. Kartalopoulos, IEEE Press, 1996.) Artificial Neural Networks are classification algorithms that consist of a collection of "nodes" (or neurons) that are arranged in complex configurations. Each node consists of a summing junction with adjustable weights (gains) for each input, a bias that is added to the input values, and a single output that is altered by a specified transfer function. The structure of a generalized node or neuron is portrayed in FIG. 5.

Figure 6:
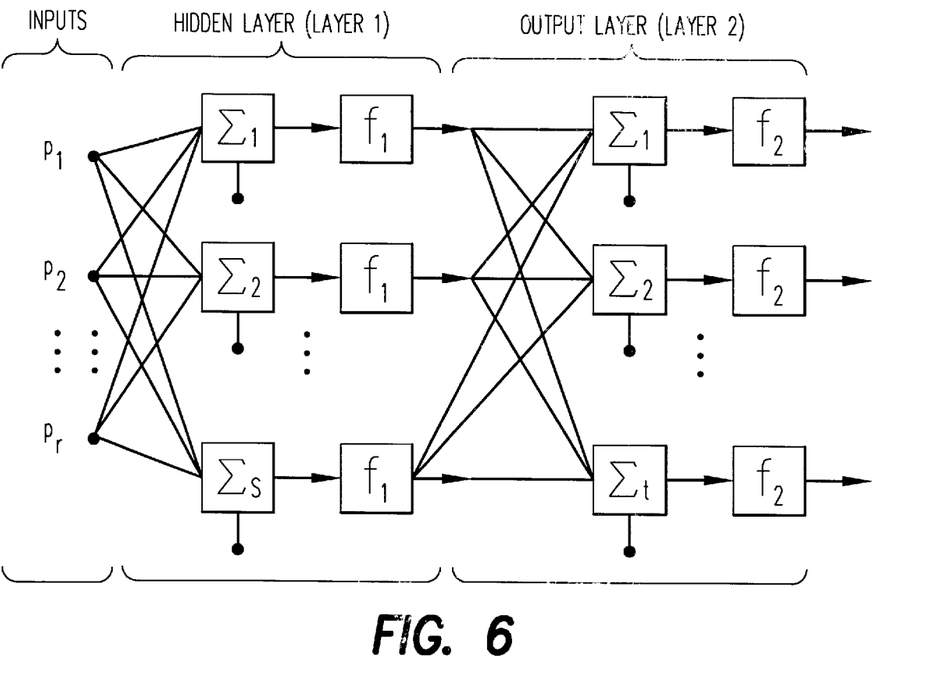
FIG. 6 is a diagram of a Feedforward Neural Network algorithm where:
  p=input to the network
  r=total number of inputs
  s=# of neurons in hidden layer
  t=# of neurons in output layer
  f=transfer function of layer
  note that the transfer function for each layer is the same for all of the neurons in that layer.

The feedforward configuration is the most commonly used Neural Network topology. Feedforward Neural Networks consist of two layers, a hidden layer and an output layer, each containing an arbitrary number of neurons that utilize the same transfer function. Each layer is fully connected to the following layer, meaning that the output of every neuron in a layer serves as an input to every neuron in the following layer. The structure of a generalized feedforward Neural Network with r inputs, s neurons in the hidden layer, and t neurons in the output layer is portrayed in FIG. 6.

Feedforward Neural Networks are often used to classify input vectors according to categories that are defined by the user. Feedforward Neural Networks are especially powerful in circumstances where there is a known correlation between input and output, but the relationship is difficult to quantify. The system is trained by applying inputs and specifying the desired output for the system. The summing weights of each of the nodes in the Neural Network are then adjusted in order to achieve the desired output. This adjustment process normally proceeds in a forward direction from input to output where minimization of error is based on the target or desired pattern. The back-propagation algorithm (Rumelhart, Hinton and Williams, 1989) has been widely used as a learning algorithm in feedforward multi-layer Neural Networks. The back propagation learning algorithm differs from other learning algorithms in that weights to minimize error between the output response and the target are calculated by moving layer by layer backward, toward the input. When the input is reached and the weights do not change (i.e. when they reach a steady state) then the algorithm selects the next pair of input target patterns and repeats the process. Responses still move in a forward direction towards the output, but the weights are calculated by moving backward. After this training has been performed, a new input will lead to an output similar to the correct output from the training set. This generalization property makes it possible to train the network on a representative set of input/target pairs and get acceptable results without training the network on all possible input/output pairs. From a practical standpoint with reference to the present invention, the system need not be trained to recognize all test inputs.

Recurrent Neural Networks utilize the same configuration as feedforward Neural Networks with the addition of a feedback connection from the outputs of the hidden layer neurons to their inputs. These networks have an advantage over feedforward Neural Networks in that they allow the input of time series of data to contribute to the classification procedure. The recurrent Neural Network implements a matching algorithm and identifies the presence or absence of a pattern in the investigated time series of the stored target vector. In order to identify temporal patterns in the EMG data within time intervals that include a variety of activities, the preferred embodiment of the device will use a recurrent Neural Network for the first classification stage. Combinations of Neural Networks can be used to perform more complex classification procedures. As an example, the outputs from several Neural Networks can serve as the inputs to another Neural Network. Each layer of cascaded Neural Networks in a Neural Network system is called a classification stage. This approach will be adopted in the preferred embodiment of the device where the first series of classifications will utilize a recurrent Neural Network system whose outputs will serve as inputs to a feedforward Neural Network system in the second classification stage.

Figure 10:
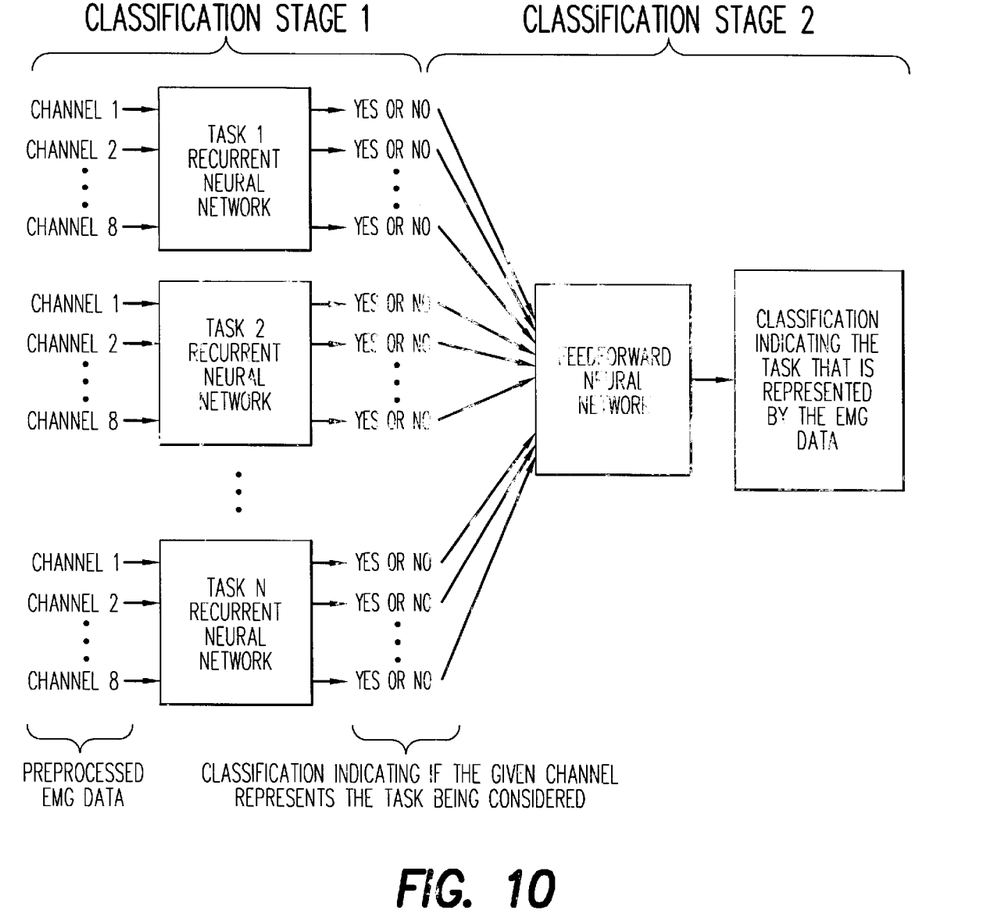
FIG. 10 is a schematic diagram of a two-stage Neural Network classification process for identifying Functional tasks.

The schematic diagram of FIG. 10 depicts the two-stage Neural Network classification process of identifying functional tasks (Tasks 1–n) on the basis of surface EMG signals (Channels 1–8). In the preferred embodiment shown, Stage I Classification is attained using a Recurrent Neural Network consisting of n layers; one for each of the n functional tasks. Pre-processed EMG signals from the eight muscle groups being monitored (Channels 1–8) provide the inputs to each layer. The outputs to each of the Neural Network layers in Stage I are depicted as "Yes or No" results, indicating whether the given channel represents the task being considered. These outputs serve as inputs to Stage II Classification, which in the preferred embodiment uses a Feedforward Neural Network consisting of only one layer. The output of this Neural Network is the classification indicating the specific task that is represented by the EMG data.

Alternatively, because the description of the EMG temporal patterns lends itself to a semi-quantitative representation, a Fuzzy-Logic based approach [Teodorescu H. N., Kandel A., Jain L. C., "Fuzzy and Neuro-Fuzzy Systems in Medicine", CRC Press, 1999] for identification of the tasks of interest can be used either in replacement of Neural Networks, or in combination with Neural Networks (Fuzzy Neural Networks are described by S. C. Lee and E. T. Lee, "Fuzzy Neural Networks", Math.Biosci., vol 23, pp. 151–177, 1975). In defining the association between EMG temporal patterns and specific tasks, it is apparent that an exact definition of the timing and amplitude of the EMG signals is not essential. In fact, the same task may be accomplished in slightly different ways, but still needs to be identified as the same task. The use of membership functions by Fuzzy-Logic systems is a powerful approach to solve this problem. Membership functions are Fuzzy Logic tools to express the extent to which a variable may be associated with a certain attribute. In the present invention, Fuzzy Logic may be used for classification of Functional Activities by defining the amplitude of the EMG signal as "small", "intermediate", "high" (fuzzy attributes). The membership function provides a number in a range that indicates the extent to which the EMG signal amplitude may be considered "small", "intermediate", and "high". The membership functions allow the system to adopt a certain "tolerance" to modifications of the temporal pattern. A fuzzy description of the EMG patterns can be input to a fuzzy c-means data clustering algorithm (Bezdek, J. C., "Pattern Recognition with Fuzzy Objective Function Algorithms", Plenum Press, New York, 1981). This technique is capable of clustering the data as described in a multidimensional space starting from an initial guess of the cluster centers and iteratively moving the cluster centers to the "right" location within the data set. This iteration is based on generating a Sugeno-type fuzzy inference system (Sugeno M., "Industrial Applications of Fuzzy Control", Elsevier Science, 1985) and the associated membership functions.

Figure 8:
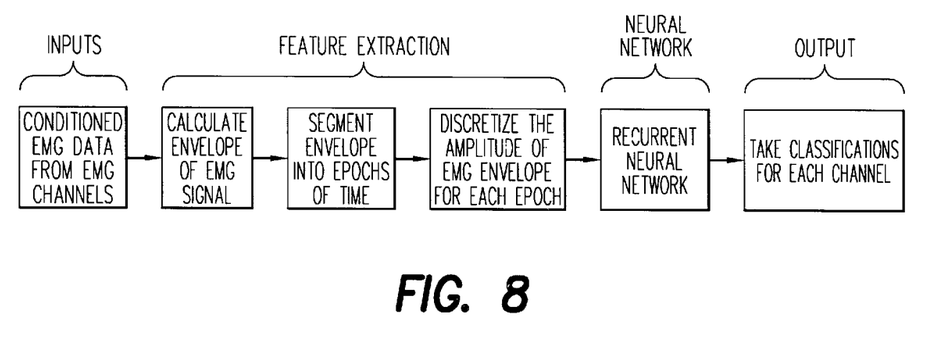
FIG. 8 is a block diagram of a first stage of developing a classification function by training an artificial as Neural Network using inputs from an EMG database.

The EMG signals that comprise the normative and patient data bases are processed in the same way by the artificial Neural Network using a two stage process (Stage I and Stage II) to set the classification functions for identification of the Functional Activities. Once these functions are developed, the system is prepared for use to monitor the activities of an intended subject. The first stage of training of the artificial Neural Network is depicted in FIG. 8 and begins with the input of the feature-extracted EMG signals from each of the eight EMG channels of the database to the input nodes of a recurrent Neural Network. The training process is one in which known data (i.e. EMG data from the data base that is known "a priori" to correspond to a specific Functional Activity) is input to the Neural Network, and it accordingly sets appropriate weightings to each of the nodes in the hidden layer to optimally match the known input to the desired output or classification of the Functional Activity. The weightings assigned to each channel are continuously updated and fully set after all of the data in the data base has been processed by the Neural Network system. Thereby, the system is optimally trained for each of the EMG channels to recognize the task. The same process is repeated for each of the specific functional motor tasks that are represented in the normative or patient data bases.

Figure 9:
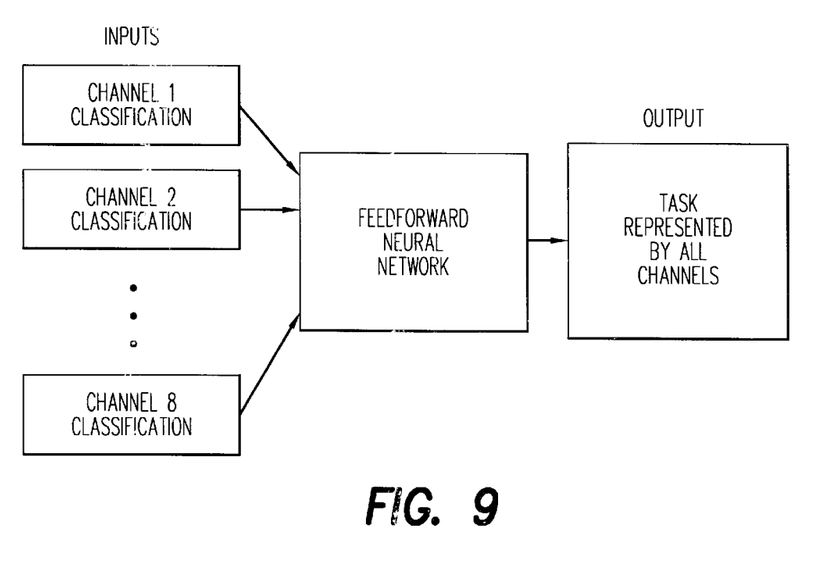
FIG. 9 is a block diagram of the second stage of developing a classification function by training an artificial Neural Network using the output from the Neural Network stage of FIG. 8 as the inputs to a second Neural Network stage.

The output channels of the Stage I classification procedure serve as the inputs to the Stage II classification process depicted in FIG. 9. An optimization process configured in the feedforward Neural Network of Stage II classification makes the identification of the desired Functional Activity on the bases of all eight channels. This Neural Network undergoes a similar "training" process as in Stage I classification, such that weights are assigned according to obtaining the best match between input and outputs of the system.

The number of EMG channels used for classification is reduced from eight to no more than four by re-processing the Neural Network system to autonomously use all combinations of outputs from the channel-specific Stage I classification Neural Network to train and test the second stage. All subsets of less than eight EMG channels will be used in evaluating the performance of the task identification system. The performance of the identification process will be evaluated based on its receiver operating characteristic (ROC). The ROC is widely used in studies involving classification and consists of a plot of the sensitivity of a system versus its specificity (Scharf LL. "Statistical Signal Processing". Reading, MA: Adisson-Wesley, 1991).

The system 11 can be used to indirectly monitor trunk, lower back, cervical, and/or limb activity for patients with spinal pain syndromes (e.g. lower back pain, cervical pain) or individuals at risk for spinal pain syndromes, or other chronic or acute pain syndromes (e.g. fibromyalgia, connective tissue disorders, repetitive-use syndromes, chronic-fatigue syndromes) during home or work-site functioning. In addition, the system can monitor home exercises as a teaching/training device (e.g. when combined with feedback) or as a means of assuring patient compliance (e.g. by tabulating the number of times a day the exercise was completed and whether the exercise was performed as prescribed) based on signals (preferably electromyographic) obtained from sensors attached to the surface of the skin at locations relative to the muscles of interest. Alternatively, the system 11 can monitor and/or warn the user of the system when they are performing physical activities that are contraindicated because of health related considerations (e.g. to prevent a back or wrist injury) while in the home, workplace, other remote location, or monitor the performance of physical activity among athletes or any individual involved in recreational or competitive sports or leisure activities as a means of enhancing training, rehabilitation, or prevention of injuries. Another advantage of the system is that it allows personal Functional Activities (e.g. toileting and dressing) to be monitored without violating a persons sense of privacy or decorum such as with the use of video based systems.

Obviously, many modifications and variations of the present invention are possible in light of the above teachings. For example, the system could employ other forms of Artificial Intelligence or knowledge-based algorithms which would include information that cannot be easily incorporated in artificial Neural Networks and Fuzzy Logic algorithms. Thus, a knowledge based system could employ commonly known information then to exclude walking as a next continuously occurring Functional Activity, after presently identifying a Functional Activity such as drinking. Also, depending on the application, the system could utilize other types of electrical sensors such as EKG or EEG, sensors, mechanical sensors such as accelerometers or goniometers, or chemical sensors such as pH or blood sensors. It is to be understood, therefore, that the invention can be practiced otherwise than as specifically described.

What is claimed is:

1. A method for remotely monitoring and identifying functional activities performed by a test subject, the method comprising the steps of:
    (a) extracting a given type of signals from each of a predetermined set of muscles of a control subject during the performance thereby of a given non-communicative functional activity;
    (b) processing said signals to provide for said signals given non-communicative parameters affected by said given functional activity;
    (c) storing data obtained in step (b);
    (d) repeating steps (a)–(c) for a plurality of other control subjects;
    (e) utilizing said data stored in steps (c) to establish a normative data base indicative of said given non-communicative functional activity;
    (f) extracting said given type of signals from each of at least some of said predetermined set of muscles of a test subject during a given monitoring period during which said test subject is engaged in a variety of functional activities including non-rebilitative functional activities; and
    (g) comparing said data base to said signals of step (f) to identify during said monitoring period portions thereof during which said test subject was performing said given non-communicative functional activity.

2. A method according to claim 1 wherein step (e) comprises passing said data through a classification algorithm to identify specific signal patterns which correspond to said given non-communicative functional activity.

3. A method according to claim 2 wherein said set includes a predetermined number of said muscles, step (e) further comprises identifying for said data base those signals extracted from a portion of said muscles having patterns most dependent on said given functional activity, and step (f) comprises extracting said signals only from said portion of said muscles.

4. A method according to claim 2 wherein said signals are biosignals.

5. A method according to claim 4 wherein said signals are EMG signals.

6. A method according to claim 5 wherein said given parameters comprise at least some taken from a group including root-mean square value, envelope, mean rectified value and frequency characteristics.

7. A method according to claim 1 wherein said set includes a predetermined number of said muscles, step (e) further comprises identifying for said data base those signals extracted from a portion of said muscles having patterns most dependent on said given functional activity, and step (f) comprises extracting said signals only from said portion of said muscles.

8. A method according to claim 7 wherein step (a) comprises attaching a sensor over each of said muscles.

9. A method according to claim 8 wherein said muscles comprise the Deltoid and the Erector Spinae.

10. A method according to claim 8 wherein said muscles comprise the Erector Spinae and a muscle in the front portion of the subject's thigh.

11. A method according to claim 8 wherein said muscles comprise the Deltoid; Erector Spinae and Vastus Lateralis.

12. A method according to claim 1 including the step of transmitting data representing the functional activities of the test subject between a location occupied thereby and a remote location for evaluation by testing personnel.

13. A method according to claim 12 wherein step (e) comprises passing said data through a classification algorithm to identify specific signal patterns which correspond to said given non-communicative functional activity.

14. A method according to claim 13 wherein said algorithm comprises a Neural Network or Fuzzy Logic technique.

15. A method according to claim 14 wherein said set includes a predetermined number of said muscles, step (e) further comprises identifying for said data base those signals extracted from a portion of said muscles having patterns most dependent on said non-communicative given functional activity, and step (f) comprises extracting said signals only from said portion of said muscles.

16. A method according to claim 1 wherein:
step (a) comprises extracting said signals from a plurality of different sets of muscles of control subjects during the performance of said variety of non-communicative functional activities;
step (b) comprises determining for said signals distinct given parameters which identify each of a plurality of predetermined ones of said non-communicative functional activities;
step (e) comprises establishing a plurality of normative data bases each indicative of a different one of said predetermined non-communicative functional activities;
step (f) comprises extracting said signals from each of at least some of said muscles of each said set; and
step (g) comprises comparing said data bases to said signals of step (f) to identify during said monitoring period portions thereof during which said test subject was performing each of said predetermined non-communicative functional activities.

17. A method according to claim 16 wherein step (e) comprises passing said data through a classification algorithm to identify specific signal patterns each of which correspond to a different one of said predetermined non-communicative functional activities.

18. A method according to claim 17 wherein each said set includes a predetermined number of said muscles, step (e) further comprises identifying for said data bases those signals extracted from a portion of said muscles from each said set patterns most dependent on said predetermined non-communicative functional activities, and step (f) comprises extracting said signals only from said portion of said muscles of each said set.

19. A method according to claim 17 wherein said signals are biosignals.

20. A method according to claim 19 wherein said signals are EMG signals.

21. A method according to claim 20 wherein said given parameters comprise at least some taken from a group including root-mean squared value, envelope, mean rectified value and frequency characteristics.

22. A method according to claim 21 wherein each said step includes a predetermined number of said muscles, step (e) further comprises identifying for said data bases those signals extracted from a portion of said muscles from each said set patterns most dependent on said predetermined non-communicative function activities, and step (f) comprises extracting said signals only from said portion of said muscles of each said set.

23. A method according to claim 21 wherein said algorithm comprises a neural Network or Fuzzy Logic.

24. A method according to claim 23 wherein each said step includes a predetermined number of said muscles, step (e) further comprises identifying for said data bases those signals extracted from a portion of said muscles from each said set patterns most dependent on said predetermined non-communicative function activities, and step (f) comprises extracting said signals only from said portion of said muscles of each said set.

25. A method according to claim 16 wherein said sets comprise muscles in at least two distinct body parts including a body part other than the forearm or hand.

26. A method according to claim 25 wherein said muscles comprise at least one shoulder muscle.

27. A method according to claim 26 wherein said muscles comprise the Deltoid.

28. A method according to claim 25 wherein said muscles comprise at least one trunk muscle.

29. A method according to claim 28 wherein said muscles comprise the Erector Spinae.

30. A method according to claim 25 wherein said muscles comprise at least one thigh muscle.

31. A method according to claim 30 wherein said muscles comprise the Lateralis.

32. A method for remotely monitoring and identifying non-communicative functional activities performed by a test subject having abnormalities of motor function, the method comprising the steps of:
(a) extracting a given type of signals from each of a predetermined set of muscles of the test subject during the performance thereby of a given non-communicative functional activity.
(b) processing said signals to provide for said signals given parameters affected by said non-communicative functional activity.
(c) storing data obtained in step (b);
(d) utilizing said data stored in step (c) to establish a normative data base indicative of said given non-communicative functional activity;
(e) extracting said given type of signals from at least some of said predetermined set of muscles of the test subject during a given monitoring period during which said test subject is engaged in a variety of functional activities including non-rebilitative functional activities; and
(f) comparing said data base to said signals of step (e) to identify during said monitoring period portions thereof during which the test subject was performing said given non-communicative functional activity.

33. A method according to claim 32 wherein step (d) comprises passing said data through a classification algorithm to identify specific signal patterns which correspond to said given non-communicative functional activity.

34. A method according to claim 33 wherein said set includes a predetermined number of said muscles, step (e) further comprises identifying for said data base those signals extracted from a portion of said muscles having patterns most dependent on said given non-communicative functional activity, and step (f) comprises extracting said signals only from said portion of said muscles.

35. A method according to claim 32 wherein:

step (a) comprises extracting said signals from a plurality of different sets of muscles of the test subject during the performance of said variety of non-communicative functional activities;

step (b) comprises determining for said signal distinct given parameters which identify each of a plurality of predetermined ones of said non-communicative functional activities;

step (c) comprises establishing a plurality of normative data bases each indicative of a different one of said predetermined non-communicative functional activities;

step (e) comprises extracting said signals from each of at least some of said muscles of each said set; and step (f) comprises said data bases to said signals of step (e) to identify during said monitoring period portions thereof during which the test subject was performing each of said predetermined non-communicative functional activities.

36. A method according to claim 35 wherein step (d) comprises passing said data through a classification algorithm to identify specific signal patens which correspond to each said predetermined non-communicative functional activity.

37. A method according to claim 36 wherein each said step includes a predetermined number of said muscles, step (e) further comprises identifying for said data bases those signals extracted from a portion of said muscles from each said set patterns most dependent on each of said predetermined non-communicative functional activities, and step (f) comprises extracting said signals only from said portion of said muscles of each said set.

38. A system for remotely monitoring a test subject during a given period during which the test subject is performing a variety of non-communicative functional activities including non-rebilitative activities, the system comprising:

a plurality of sensors for providing signals in response to muscle activity, said sensors adapted for placement to extract said signals from predetermined muscles of the test subject;

processing means for determining certain parameters of said signals;

computer means programmed with a data base cataloging different patterns of said paramereters each produced by only specific predetermined ones of said non-communicative functional activities of the test subject, said computer means adapted to compute during said given monitoring period those portions thereof during which the test subject was performing each of said specific predetermined ones of said non-communicative functional activities; and transmission means for transmitting data representing the non-communicative functional activities performed by the test subject between a location occupied by the test subject and a remote location for evaluation by testing personnel.

39. A system according to claim 38 wherein said sensors are adapted for attachment to the test subjects skin portions overlying the muscles, said processing means is carried by each said sensor, said computer means is in the location occupied by the test subject, and including repeater means adapted to be carried by the test subject and to transmit signals between said sensors and said computer means.

40. A system according to claim 39 wherein said transmission means comprises a telephone and/or Internet link between said computer means and said remote location.

41. A system according to claim 38 wherein said data base is established by a pattern classification algorithm.

42. A method according to claim 41 wherein said algorithm comprises a Neural Network or Fuzzy Logic technique.

43. A method according to claim 42 wherein said signals are biosignals.

44. A method according to claim 43 wherein said signals are EMG signals.

\* \* \* \* \*